(«12») United States Patent
Puchhammer

(10) Patent No.: US 9,861,500 B2
(45) Date of Patent: Jan. 9, 2018

(54) PROSTHETIC GRIP UNIT

(75) Inventor: Gregor Puchhammer, Vienna (AT)

(73) Assignee: OTTO BOCK HEALTHCARE GMBH, Vienna (AT)

( * ) Notice: Subject to any disclaimer, the term of this patent is extended or adjusted under 35 U.S.C. 154(b) by 720 days.

(21) Appl. No.: 12/671,104

(22) PCT Filed: Jul. 10, 2008

(86) PCT No.: PCT/EP2008/005636
§ 371 (c)(1),
(2), (4) Date: Jan. 28, 2010

(87) PCT Pub. No.: WO2009/015751
PCT Pub. Date: Feb. 5, 2009

(65) Prior Publication Data
US 2010/0198362 A1    Aug. 5, 2010

(30) Foreign Application Priority Data
Jul. 30, 2007   (DE) ................. 10 2007 035 965

(51) Int. Cl.
*A61F 2/58*  (2006.01)
*A61F 2/68*  (2006.01)
*A61F 2/72*  (2006.01)
*A61F 2/50*  (2006.01)
*A61F 2/70*  (2006.01)

(52) U.S. Cl.
CPC ............... *A61F 2/588* (2013.01); *A61F 2/68* (2013.01); *A61F 2/72* (2013.01); *A61F 2002/5089* (2013.01); *A61F 2002/6836* (2013.01); *A61F 2002/6845* (2013.01); *A61F 2002/701* (2013.01)

(58) Field of Classification Search
CPC .... A61F 2002/701; A61F 2/586; A61F 2/588; A61F 2002/30523
USPC ........................................................... 623/64
See application file for complete search history.

(56) References Cited

U.S. PATENT DOCUMENTS

| | | | | |
|---|---|---|---|---|
| 2,573,351 A | * | 10/1951 | Motis ..................... | A61F 2/588 |
| | | | | 623/64 |
| 2,640,994 A | * | 6/1953 | Alderson ........................ | 623/24 |
| 3,693,759 A | * | 9/1972 | Schindel ................... | F03G 1/00 |
| | | | | 185/40 B |
| 3,735,426 A | * | 5/1973 | Horvath ......................... | 623/65 |
| 3,766,686 A | * | 10/1973 | Sheckells ......................... | 49/43 |
| 3,987,498 A | * | 10/1976 | Mason ............................ | 623/24 |

(Continued)

FOREIGN PATENT DOCUMENTS

| | | |
|---|---|---|
| GB | 2 109 245 | 11/1982 |
| RU | 1836061 C1 | 8/1993 |

(Continued)

*Primary Examiner* — Bruce E. Snow
*Assistant Examiner* — Melissa Hoban
(74) *Attorney, Agent, or Firm* — Whitham, Curtis & Cook, P.C.

(57) ABSTRACT

The invention relates to a prosthetic grip unit (1) having a base body (2) on which connection means (3) are disposed for fastening said grip unit to an upper extremity, at least two extensions (10, 20) protruding from said connection means, a first extension (10) being movable relative to the second extension (20) from a protruding position into a flush position, wherein the pivot axis (14) has a perpendicular orientation to the base body (2) and the first extension (10) is motor driven.

23 Claims, 7 Drawing Sheets

(56) References Cited

U.S. PATENT DOCUMENTS

| | | | |
|---|---|---|---|
| 4,094,016 A * | 6/1978 | Eroyan | 623/24 |
| 4,114,464 A | 9/1978 | Schubert et al. | |
| 4,377,305 A * | 3/1983 | Horvath | 294/106 |
| 4,685,925 A | 8/1987 | Childress et al. | |
| 4,808,187 A | 2/1989 | Patterson et al. | |
| 4,834,443 A * | 5/1989 | Crowder et al. | 294/106 |
| 5,013,326 A | 5/1991 | Horvath | |
| 6,358,285 B1 * | 3/2002 | Chen | 623/64 |
| 6,423,099 B1 * | 7/2002 | Iversen et al. | 623/64 |
| 6,921,419 B2 * | 7/2005 | Weir et al. | 623/64 |
| 2009/0192619 A1 * | 7/2009 | Martin et al. | 623/18.11 |
| 2010/0234967 A1 * | 9/2010 | Whiteley et al. | 623/24 |

FOREIGN PATENT DOCUMENTS

| | | |
|---|---|---|
| SU | 2110235 C1 | 5/1991 |
| WO | EP 0 261 276 | 9/1986 |
| WO | EP 0352251 | 1/1990 |
| WO | EP 1 277 451 | 7/2002 |

\* cited by examiner

PROSTHETIC GRIP UNIT

This application is a 371 of international application PCT/EP2008/005636, filed Jul. 10, 2008, which claims priority to European application 10 2007 035 965.0, filed Jul. 30, 2007, each of which are incorporated herein by reference.

BACKGROUND OF THE INVENTION

Field of the Invention

The invention relates to a prosthetic grip unit with a base body of which connection means for attaching said grip unit to an tipper extremity are arranged, with at least two members protruding from said base body, a first member of the members being movable mounted such that relative to the second member it can be displaced from a protruding into a flush position. In particular, the invention relates to so-called hooks which constitute a simple and stable grip device. Here, the pivot axis of the movable member is aligned perpendicularly to the base body which emulates metacarpus of a natural hand.

Background Description

The prior art has known such prosthetic grip units for quite some time, for example they are described in GB 2 109 245 A1. In order to move the member movably mounted on the tease body in the direction of a fixed second member, an elastic hand which is dimensioned such that the two members are brought into a flush position is arranged at the proximal end of the two members. The movably mounted member is displaced into a splayed, position using a Bowden cable. The resilient force moves the member in the direction, of the fixed member and objects can be held there by said member. The disadvantage of these mechanically simple and robust grip devices is that the gripping force is limited by the pretension or the elastic band. Furthermore, relatively large forces have to be applied by the wearer of the prosthetic grip unit for splaying the movable member.

SUMMARY OF THE INVENTION

An object of the present invention is to provide a prosthetic grip unit which is more comfortable to use for the prosthesis user.

According to the invention, this object is achieved by a prosthetic grip unit with the features of claim 1.

Advantageous refinements and developments of the invention are listed in the dependent claims.

In the prosthetic grip unit with a base body on which connection means for attaching said grip unit to an upper extremity are arranged, with at least two members protruding from said base body, a first member of the members being movably mounted such that relative to the second member it can be displaced from a protruding into a flush position, and with the pivot axis thereof being aligned perpendicularly to the base body, provision is made for the first member to be driven by a motor. The motor-driven actuation of the movably mounted member allows quick and controlled actuation which is independent of the elastic pretension by an elastic band and so a high gripping force can be achieved independently of the spring pretension. Thus, the user no longer needs to apply a correspondingly high opening force in order to be able to hold an object with a sufficiently high gripping force. The motor-driven drive allows fast actuation add selective switching of the grip device into an opened or closed rest position.

Provided that the second member is rigidly attached to the base body, or formed integrally thereon, a simple structural assembly can be achieved by only one member having to be coupled to the drive. However, in principle, provision is also made fox the second member to be driven by a motor and so both members are mounted such that they can move with respect to one another.

In order to match the respective member to the desired application, or in order to be able to replace damaged members, said members are attached to the base body in an interchangeable fashion, e.g. they are screwed into the base body or attached thereon using a karabiner look. This affords the possibility of applying suitable members for the respective application.

The base body is preferably designed as the housing for the drive and so the drive is arranged within the base body. In particular, an electric motor is provided as a drive and said motor can be or is directly connected to the movably mounted member. The movably mounted member can likewise be coupled to the drive or electric motor via a gearbox in order to bring about a desired transmission and, as a result of this, an adjustment either in the displacement speed or in the gripping force.

A space-saving refinement of the invention provides for the drive to be mounted in the base body and the first member to be mounted on the bearing of the drive in order to be able to provide for the movable member a bearing which is as large and stable as possible.

The members can have a hook-shaped design in order to be able to provide much variation in the application options. A third member can be rigidly attached to the first member or be formed thereon in order to provide an additional support option for gripped objects. Such a third member is provided in particular for supporting a pen or another tool, which is champed between the two members. Here, the first member is preferably arranged between the second and the third member and protrudes laterally, e.g. at a right angle, from the first member. The third member can likewise have a bend to avoid slippage of the object placed thereon.

A receptacle for a storage device for electrical energy is arranged on the base body and so an energy storage unit can easily be replaced. Its energy storage unit, e.g. a rechargeable battery, can easily be coupled to the base body, for example via a screw mechanism or a karabiner lock, and therefore a replacement battery or a replacement accumulator can quickly be exchanged.

The motorized actuation of the movably mounted member allows controlling the latter by myoelectric pulses, for which purpose provision is made for a corresponding myoelectric control of the drive. Thus, the actuation of the grip unit does not require a projecting movement of the shoulder, but can be performed via myoelectric pulses. So as to be able to operate the drive, in particular the motor, based on myoelectric pulses, control electronics for the drive are arranged, preferably encapsulated, in the base body and so the electrodes or myoelectric pulse generator still only have or has to be coupled thereto in order to start operation of the prosthetic grip unit. The control can also be arranged in the energy storage or be situated within the drive.

Both the control unit and the drive are encapsulated in a waterproof fashion in order to ensure functional reliability even when using the prosthetic grip unit in harsh surroundings.

In order to achieve a design that is as compact as possible, the drive axle of the drive or motor is oriented in parallel (in particular coaxially) to the pivot axis of the first member and so a direct coupling without an angle gearbox is possible. Should a gearbox stage have to be interposed, it can easily be arranged and designed in a coaxial fashion.

In order to continue to ensure the functionality if the motor or the energy supply fails, the drive is deigned such that is can be decoupled from the first member. A conventional force storage element, e.g. in the form of an elastic band, can then be placed around the members in order to provide the necessary gripping force. For this, holding devices for a corresponding spring element, e.g. receptacles for an elastic ring or a tension spring, are formed on the first member and the second member.

In a development of the invention, an actuation lever can be mounted on the third member and is coupled to the wearer of the prosthetic grip unit via a Bowden cable mounted in a longitudinally displaceable fashion. The prosthesis user can bring about the actuation of the members in a conventional fashion using this actuation lever if no myoelectric coupling is provided. The longitudinally displaceable mounting allows fitting to the bodily conditions of the prosthesis user. Here, the actuation is generally performed by a movement of the shoulder and so a prostheses user with a large radius of movement prefers an arrangement of the Bowden cable at the distal end of the third member, while a proximal arrangement of the Bowden cable on the lever should be selected in the case of a less of movement or a small range of motion due to physiological conditions.

A development of the invention provides for there to foe at least one sensor unit for defecting the actuation element of the actuation lever and for said sensor to foe coupled to the actuation lever, and therefore the gripping force can be controlled as a function of the actuation force and the actuation moments exerted by the actuation lever. The higher the actuation forces are, the higher the gripping force is set and so a matched gripping force can be set between the two members lying against one another. A sensor can likewise be present for determining the current gripping force, said sensor transmitting a response thereof to the control unit and locking the drive or ensuring that the gripping force is maintained.

So that fundamental settings for the closing fores or the speed of the pivot movement can be undertaken, provision is made on the base body or the energy storage unit for adjustment devices which are preferably arranged on the back side of the grip unit which corresponds to the back of the hand in order to be able to bring about a simple adjustment by the prosthesis user. The drive has a reversible design so as to enable it to open and close the grip unit. Adjustment devices or adjustment apparatuses for switching a mode can likewise foe provided, wherein these devices allow a switch between different types of control, for example between a force control, a position control, an EVC (electronic voluntary opening) or an EVC (electronic voluntary closing) control. The adjustment devices can bring about both the mode switch and the force or speed settings.

In order to decouple the first member from the drive, the first member is coupled to the drive via a displaceable toothing and so an adjustment which is independent of the drive is possible when the toothing is disengaged from the drive.

In a development of the invention, provision is made for the drive to have a power gear and a speed gear, with it being possible to mechanically or electrically switch therebetween. As a result, a speedy displacement of two members toward each other can firstly foe made possible by a high transmission which produces a relatively low gripping force.

If the members come into contact with the object to be gripped, the gripping force is automatically increased while the gripping speed is reduced. This switch can foe performed by purely mechanical means using a corresponding clutch or by means of an electronic control.

Exemplary embodiments of the invention will foe explained in the following figures. In the figures, the same reference signs denote the same components or components with the same effect. In detail,

DETAILED DESCRIPTION THE INVENTION

Figure 1:
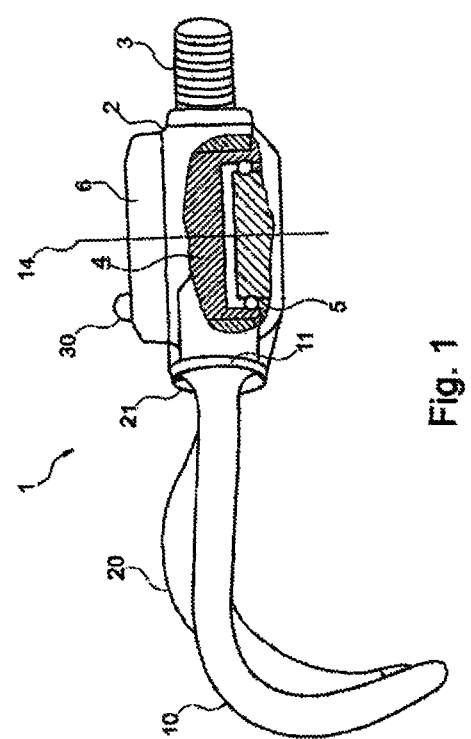
FIG. 1 shows a partial sectional view of a grip device.

FIG. 1 illustrates in a partial sectional view a prosthetic grip unit 1 with a base body 2 which is preferably produced of a metal, in particular a light metal. On the base body 2, provision is made for a connection means 3 in the form of a thread as a standard connection for the prosthetic grip unit to e.g. a lower arm prosthesis or to a receptacle apparatus attached to a lower arm. In particular, the connection means 3 are designed as a helical thread. The connection means 3 can have a deviating embodiment, for example as a bayonet connector or the like.

A drive 4 in the form of an electric motor with a flat design is arranged within the housing 2. The base body 2 forms a frame or a chassis for both the connection means 3 and for two members 10, 20, the first member 10 of which members is, in the illustrated exemplary embodiment, mounted on the base body 2 such that it can pivot. The second member 20 is fixedly attached to the base body 2; in particular, said member is screwed thereon or insert eel into a receptacle and secured therein. Within the base body 2, the drive 4 as an electric motor is mounted by a bearing 5 which at the same time constitutes the central bearing for the movable member 10.

As an alternative to a fixed embodiment of the second member 20, the latter can likewise foe driven via the drive 4 and be moved relative to the first member 10. Here, the pivot movement is performed over the pivot axis 14 which runs perpendicular to the base of the drive 4 and preferably runs parallel, in particular coaxially, to the rotational axle of the drive 4. The pivot axis 14 in this case runs perpendicular to that surface which, on a natural hand, would correspond to the palm of the hand or the back of the hand. The two members 10, 20 can foe moved into an open position or into a position where they lie against one another in order to be able to grip objects or clamp them therebetween in the position where said members lie against one another. The members 10, 20 are preferably bent at the distal ends thereof and thus designed as a hook since this geometry has proven to be particularly suitable for simple gripping performances.

A battery 6 or an accumulator is attached to the upper side of the base body 2 and it is mounted on the base body 2 in a replaceable fashion. On the replaceable accumulator 6, provision can foe made for adjustment devices which can adjust the speed of the displacement and the gripping force to be applied between the members 10, 20. The reference sign 30 denotes a tip of a third member which is concealed by the main drive 4 in this perspective.

Projections 11, 21 are formed at the proximal ends of members 10, 20; said projections serve as barriers for an elastic band 8 and so the latter is securely held on the members 10, 20 and secured against slippage in the distal direction.

Figure 2:
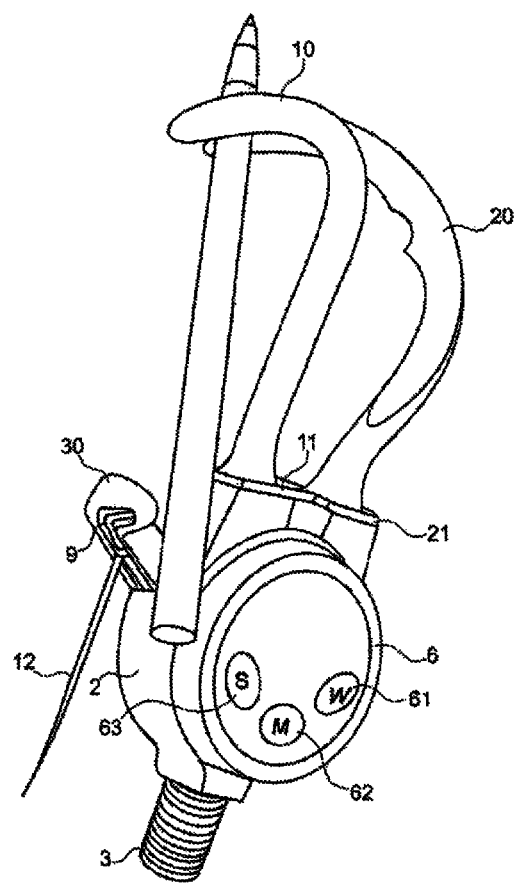
FIG. 2 shows a perspective oblique plan view of a first variant.

FIG. 2 illustrates a perspective oblique plan view of the grip unit 1 and herein it can be seen that a third member 30 is arranged on the first member 10 and it exercises the function of the thumb or a rest for an object to be gripped (which is a pen in the illustrated exemplary embodiment). The third member 30 is, together with the first member 10, mounted on the base body 2 such that if can pivot the receptacle for the first member 10 preferably forms an integral component together with the third member 30. Alternatively, the third member 30 can also foe screwed in or inserted.

In the illustrated exemplary embodiment, the second member 20 is fixed and is attached to the base body 2 in a replaceable fashion.

The connection means 3 can be replaced by a myoelectric connection piece which requires the provision of additional cabling to the drive 4. In the case of a myoelectric connection piece, the cabling is preferably guided through the connection means 3.

On the upper side of the prosthetic grip unit 1, and there on the upper side of the energy store 6, sensor surfaces 62, 62, 63 are available as adjustment devices for the maximum active closing force of the members 10, 20 and possibly for the closing speed.

An actuation lever 9 is arranged within the third member 30 and it is actuated via a Bowden cable 12 which is mounted in a displaceable and fixable fashion on the actuation lever 9. The Bowden cable 12 is arranged on the upper arm or the shoulder of the prosthesis user and brings about an actuation of the motor 4 when the shoulder is actuated and thus brings about a closing or an opening of the members 10, 20. The opening can be performed by a repeated actuation of the Bowden cable 12. For this, provision is made for the drive 4 to have a reversible design.

Figure 3:
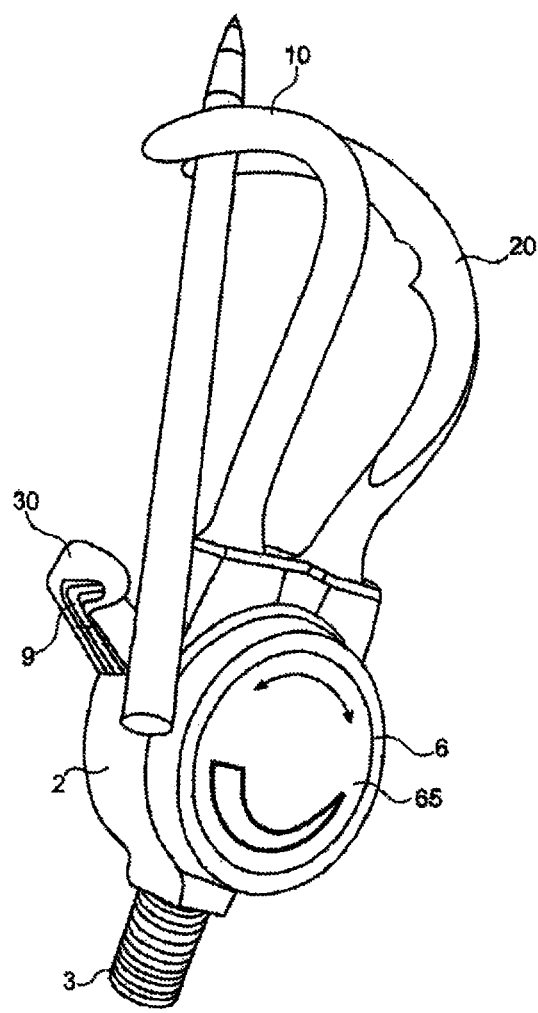
FIG. 3 shows a perspective oblique plan view of a second variant.

A variant of the embodiment as per FIG. 2 is illustrated in FIG. 3, in which a rotatable cover cap 65 brings about an adjustment rather than puctiform sensor fields 61, 62, 63. The ability to rotate in both directions is indicated by the double-headed arrow. The gripping force is increased in the case of a clockwise rotation; by contrast, a counterclockwise rotation reduces the gripping force.

Furthermore, additional sensor fields or adjustment options, e.g. for the displacement velocities or a switching of the control modes, can be arranged on the rear side of the accumulator 6. It is likewise possible for the sensor fields to be arranged laterally on the housing 2 instead of on the rear side or upper side of the grip unit 1.

Figure 4:
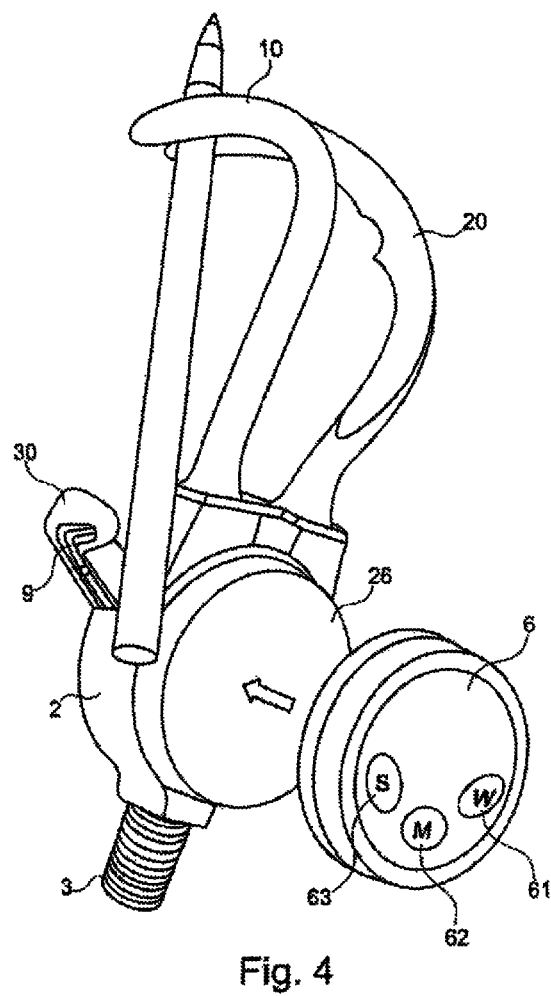
FIG. 4 shows a grip device as per FIG. 2 with an unmounted energy storage device.

FIG. 4 illustrates a variant of FIG. 2 in which the storage device 6 for electrical energy, as a replaceable capsule, can be affixed to the rear side of the grip unit 1 at a correspondingly designed receptacle 26. The storage device 6 is fixed by screwing or by alternative, in particular interlocking, attachment means. Since the storage device 6 can be replaced, the independence of the prosthesis user can be increased because longer times of operation can be made possible fey a simple and quick exchange of the accumulator 6. The accumulator 6 itself has a waterproof design and has a likewise waterproof contact with the drive 4. A further sensor system can likewise foe arranged on the rear side of the grip unit 1 or in the accumulator 6, wherein the view onto the respectively gripped object is hardly adversely affected, by arranging the accumulator 6 on the rear side.

The integration of the accumulator 6 in the grip unit 1 can provide an autonomous grip system which can easily be replaced by a conventional, mechanical grip system. The Bowden cable 12 can be arranged such that a readjustment or deflection of the cables is unnecessary and so a simple replacement of the motor-driven grip unit 1 by conventional systems is easily possible.

Figure 5:
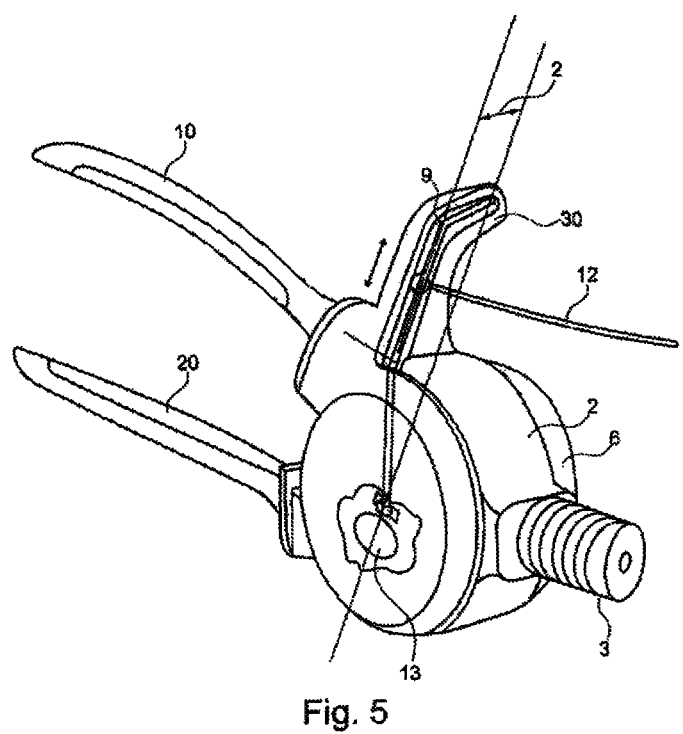
FIG. 5 shows a perspective oblique view from below.

FIG. 5 illustrates the underside of the grip unit 1 and the actuation lever 9 and the functionality thereof can be recognized en the basis thereof. The Bowden cable 12 can foe mounted in a displaceable fashion on the actuation lever 9 (as indicated by the double-headed arrow) via a ball-shaped termination piece or clamping devices. Thus, the Bowden cable 12 is fixed to the actuation lever 9 in a displaceable fashion. A sensor device 13 which measures the actuation moment on the actuation lever 9 is arranged on the underside of the housing 2 or within the housing 2. The lever arm L which is formed by the actuation lever 9 or the point of application of the Bowden cable 12 along the displacement path thereof affords the possibility of the sensor signal of the sensor 13 being independent of the position of the end piece of the Bowden cable 12 on the actuation lever 9, which signal is produced by tension within the Bowden cable 12. This affords the possibility or providing a sensor signal by the sensor unit 13 which is proportional to the tension of the Bowden cable 12. Therefore, the point of application of the Bowden cable 12 can be selected at an arbitrary point within the displacement range, wherein the receptacle of the Bowden cable 12 in the connection piece or in the clamping apparatus is selected such that the motor-driven grip unit 1 can quickly be replaced by a conventional grip unit. The second mounting point of the actuation lever 9 is in the upwardly bent end of the third member 30, in the so-called thumb.

Figure 6:
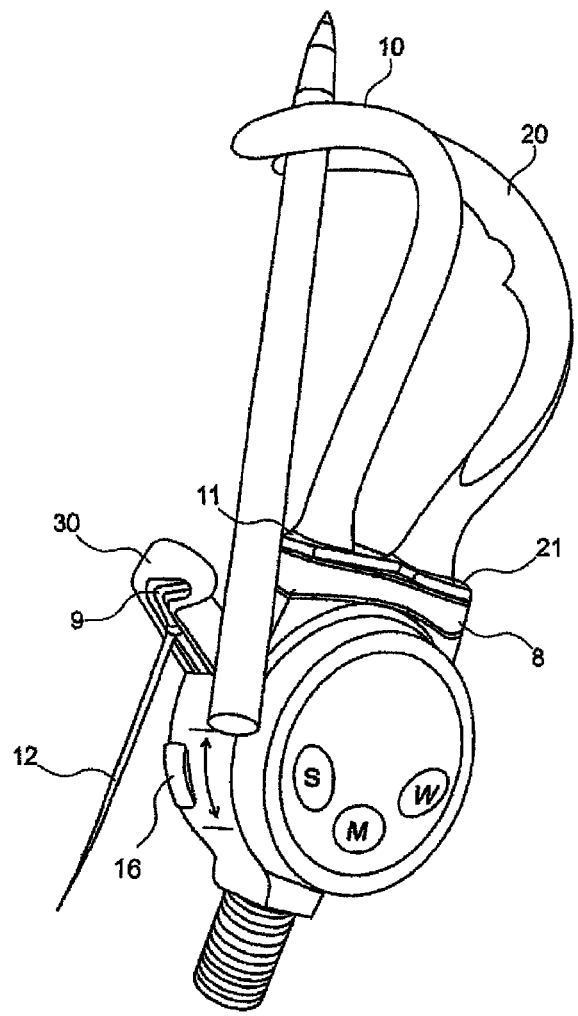
FIG. 6 shows a variant of FIG. 2 with an unlocking mechanism.

FIG. 6 shows a variant of the invention in which a safety device is integrated which allows manual opening of the members 10, 20 in the case of an electrical malfunction of the prosthetic grip unit. By displacing the adjustment device 16, a planned toothing in the interior of the drive 4 is disengaged and so the movably mounted member 10, and hence the third member 30, is released. The actuation element 14 is effective in both displacement directions and so the displacement can also be brought about in both directions. Provided that the members 10, 30 mounted, such that they can pivot are decoupled from the drive 4, a tree mobility can be implemented. In order to allow the members 10, 20 to close, provision is made for a spring element 8 in the form of an elastic ring or an elastic band, which is attached as a stopgap solution for providing the closing force. The projections 11, 21 prevent slippage from the members 10, 20. By means of the Bowden cable 12 and the correspondingly stably designed actuation lever 9, the grip device 1 can also be actuated without energy supply or in the case of an electrical malfunction and so there is emergency operation even though this loses the advantages according to the invention.

Control devices for a myoelectric control can foe arranged within the housing 2; the control device can also be integrated separately within the accumulator 6. The gripping force can be adjusted by means of a potentiometer, as can likewise the speed of the closing or opening movement. As an alternative to this, provision is made for a mechanical control via the actuation of the actuation lever 9 and an actuation by the shoulder.

The respective position of the members 10, 20, 30 can be determined by sensors and so the rotational movement of rite drive 4 can be correctly assigned when a myoelectric signal is applied. The rest position of the grip unit can be selected freely, either open with moved-apart members 10, 20 or closed. A proprioceptor sensor system allows the provision of an adapted gripping force. Whereas conventional mechanical grip units are opened by a force on the Bowden cable against a spring force, this can foe performed relatively straightforwardly in an electromotive fashion by means of a simple signal. The purely mechanical opening of the grip unit requires double to four times the force, in terms of tension on the Bowden cable, available at the tip of the members 10, 20. Therefore, the actuation path is correspondingly small and is applied by a shoulder pull. In the case of a purely mechanical solution, the attainable gripping force is defined, and set by the strength of the spring or the elastic band and the lever transmission. The option to be driven by motor and a force-dependent control affords the possibility of matching the forces to be produced on the members to the actuation forces, but to decouple them in respect of their magnitude. Larger forces on the actuation lever 9 lead to an increased closing force, but the level of the closing force can be set independently of the strength of the actuation force. As a result, the actuation force is decoupled, from the actuation path since there is a sensor system for measuring the force within the Bowden cable 12. This is important for an adjustment in respect of the patient because the different physiological conditions can be taken into account. The actuation path for the complete opening of the members 10, 20 is determined by the position of the Bowden cable 12 on the actuation lever 9. A connection point in the vicinity of the first member 10, i.e. near the center of rotation, is selected for petite persons or persons with a reduced mobility, while a connection point for the Bowden cable which is as distal as possible is provided for large persons with much mobility in the region of the shoulder.

Provision can be made for a corresponding control, in which the grip unit closes in principle until the set force or the set moment is reached. This set force can be many times larger than what is conventional or possible in the previous mechanical grip units.

Figure 7:
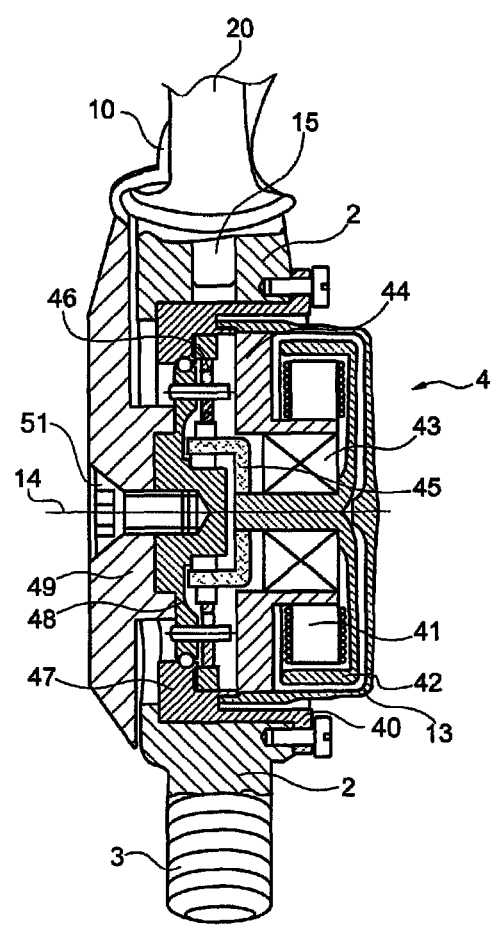
FIG. 7 shows a sectional illustration of the bearing.

FIG. 7 shows the bearing of the movable member 10 on the base body 2 in a sectional illustration. The entire drive 4 with a motor having a stator 41 and a rotor 42 is mounted within the base body 2. A cover cap 13 covers the drive 4 toward the outside. The rotor 42 rotates about the pivot axis 14 and is mounted in a rotor bearing 43. Arranged within the base body 2 and the drive 4 there are motor and control electronics 44 by means of which different movement modes or speeds and/or gripping forces can be set. An eccentric 45 with a coupling part to the rotor 42 is used to connect the rotor to a cycloid disk 46 which is coupled to a driven dish 48 by pins. The driven disk 48 is mounted on the outer race of the main bearing 47 and is connected to a disk 49 which is mounted movably with respect to the base body 2 and to which is the movable member 10 is attached. The disk 49 is secured on the driven disk 48 by a screw 51. A support 14 secured in the base body 2 by screws is used to hold the main bearing 47 in the base body 2. In the process, the support 40 presses against the bearing outer race of the main bearing 47.

It can be seen at the upper end of FIG. 7 that the fixed member 20 is attached, e.g. screwed or clamped, to the base body 2 by a stud 15. In the illustrated exemplary embodiment, the drive 4 and the movable member 10 are together mounted on the base body 2 via the main bearing 47.

The invention claimed is:

1. A prosthetic grip unit, comprising:
   a base body having a connection device for attaching said grip unit to an upper extremity prosthesis;
   at least two members protruding from said base body, a first member of the at least two members being movably mounted such that relative to a second member of the at least two members, the first member is displaceable with respect to the second member and allows movement of the first member toward the second member, and the first member having a pivot axis aligned perpendicularly to the base body, wherein the second member is fixedly attached to the base body;
   an electric motor mounted within the base body and connected to drive the first member;
   a driven disk that is mounted on an outer race of a main bearing, wherein the motor drives the driven disk; and
   a further disk connected to the driven disk, wherein the first member is rigidly secured with respect to the driven disk via the further disk.

2. The prosthetic grip unit as claimed in claim 1, wherein the second member is attached to the base body in an interchangeable fashion.

3. The prosthetic grip unit as claimed in claim 1, wherein the first and second members have a hook-shaped design.

4. The prosthetic grip unit as claimed in claim 1, further comprising a third member rigidly attached to the first member or formed thereon.

5. The prosthetic grip unit as claimed in claim 1, further comprising a third member, wherein the first member is arranged between the second and the third member.

6. The prosthetic grip unit as claimed in claim 1, further comprising a receptacle for a storage device for electrical energy provided on the base body.

7. The prosthetic grip unit as claimed in claim 1, further comprising a myoelectric control of the motor.

8. The prosthetic grip unit as claimed in claim 1, further comprising control electronics for the motor arranged in the base body.

9. The prosthetic grip unit as claimed in claim 1, further comprising control electronics provided in the motor.

10. The prosthetic grip unit as claimed in claim 1, wherein the motor is encapsulated to be waterproof.

11. The prosthetic grip unit as claimed in claim 1, wherein the motor has a drive axle and the drive axle of the motor is oriented in parallel or coaxially to the pivot axis of the first member.

12. The prosthetic grip unit as claimed in claim 1, further comprising an adjustment device arranged on the base body for adjusting the closing force and/or speed of the pivot movement of the first member.

13. The prosthetic grip unit as claimed in claim 1, further comprising an adjustment device arranged on the base body for switching a mode of operation.

14. The prosthetic grip unit as claimed in claim 1, wherein the motor can be driven reversibly.

15. The prosthetic grip unit as claimed in claim 1, further comprising a power gear and a speed gear connected to the motor, wherein the power gear and the speed gear can be mechanically or electrically switched there between.

16. The prosthetic grip unit as claimed in claim 1, wherein the motor can be decoupled from the first member.

17. The prosthetic grip unit as claimed in claim 1, further comprising holding devices and a spring element, wherein the holding devices securely hold the spring element and are arranged on the first member and the second member.

18. The prosthetic grip unit as claimed in claim 1, further comprising a third element having mounted thereon an actuation lever coupled to a wearer of the prosthetic grip unit via a Bowden cable mounted in a longitudinally displaceable fashion.

19. The prosthetic grip unit as claimed in claim 1, further comprising an actuation lever mounted to the grip unit and a sensor unit mounted within the base body, the sensor unit detecting an actuation moment of the actuation lever.

20. The prosthetic grip unit as claimed in claim 1, further comprising a displaceable toothing, wherein the first member is coupled to the motor via the displaceable toothing, and the toothing can be brought to disengage from the motor.

21. The prosthetic grip unit as claimed in claim 1, wherein the first member is mounted on the main bearing in an interchangeable fashion.

22. The prosthetic grip unit as claimed in claim 1, wherein the second member is formed integrally on the base body.

23. The prosthetic grip unit as claimed in claim 1, wherein the driven disk is mounted on the outer race of the main bearing with rolling elements, and wherein the further disk is adjacent to the driven disk.

\* \* \* \* \*